(12) United States Patent
Kozak

(10) Patent No.: US 10,034,729 B2
(45) Date of Patent: Jul. 31, 2018

(54) DENTAL TAPE AND FLOSS HOLDER WITH INSTALLATION CASSETTE

(76) Inventor: Roman Kozak, Cranford, NJ (US)

( * ) Notice: Subject to any disclaimer, the term of this patent is extended or adjusted under 35 U.S.C. 154(b) by 988 days.

(21) Appl. No.: 13/825,321

(22) PCT Filed: Sep. 18, 2011

(86) PCT No.: PCT/US2011/052066
§ 371 (c)(1),
(2), (4) Date: Apr. 9, 2015

(87) PCT Pub. No.: WO2012/040070
PCT Pub. Date: Mar. 29, 2012

(65) Prior Publication Data
US 2014/0290691 A1 Oct. 2, 2014

Related U.S. Application Data

(60) Provisional application No. 61/403,635, filed on Sep. 20, 2010.

(51) Int. Cl.
*A61C 15/04* (2006.01)

(52) U.S. Cl.
CPC .......... *A61C 15/043* (2013.01); *A61C 15/046* (2013.01)

(58) Field of Classification Search
CPC ....... A61C 15/00; A61C 15/04; A61C 15/043; A61C 15/045; A61C 15/046; A61C 15/047; A61C 15/048; B65H 23/18; G11B 15/43
USPC .................................................. 132/323–327
See application file for complete search history.

(56) References Cited

U.S. PATENT DOCUMENTS

| | | | | |
|---|---|---|---|---|
| 3,789,859 A * | 2/1974 | Chambers | ............ | A61C 15/046 132/326 |
| 3,882,879 A * | 5/1975 | Lucas | ............ | A61C 15/046 132/325 |
| 3,924,647 A * | 12/1975 | Lindblad | ............ | A61C 15/046 132/326 |
| 4,308,880 A * | 1/1982 | Graves | ............ | A61C 15/043 132/321 |
| 4,901,742 A * | 2/1990 | Olson | ............ | A61C 15/046 132/325 |
| 5,269,331 A * | 12/1993 | Tanriverdi | ............ | A61C 15/046 132/325 |
| 5,301,699 A * | 4/1994 | Craft | ............ | A61C 15/046 132/325 |

(Continued)

*Primary Examiner* — Tatiana Nobrega
*Assistant Examiner* — Jennifer Gill
(74) *Attorney, Agent, or Firm* — Law Offices of Leo Mikityanskiy, P.C.; Leonid Mikityanskiy

(57) ABSTRACT

An apparatus includes a bottom portion comprising a spindle for receiving a quantity of floss. A first locking plate is operable for receiving a feed portion of the floss upon a horizontal surface. A plate extends from the first locking plate where a distal end of the plate engages the feed portion and a return portion of the feed portion returns back over the horizontal surface. An aperture enables an exiting portion of the return portion to exit the bottom portion. A top portion includes a spindle cap portion operable for engaging the spindle. A second locking plate is operable for engaging the first locking plate to substantially constrain the feed portion of the floss and the return portion. A stretching mechanism is joined to the second plate for applying a stretching force along a portion of the feed portion and a portion of the return portion.

20 Claims, 7 Drawing Sheets

(56) References Cited

U.S. PATENT DOCUMENTS

| | | | |
|---|---|---|---|
| 5,613,508 A * | 3/1997 | Bushman | A61C 15/046 132/325 |
| 6,079,424 A | 6/2000 | Lillbacka | |
| 6,363,949 B1 * | 4/2002 | Brown | A61C 15/046 132/324 |
| 2003/0029472 A1 * | 2/2003 | Adler | A61C 15/046 132/325 |
| 2005/0000539 A1 | 1/2005 | Berman et al. | |
| 2005/0247328 A1 * | 11/2005 | Shen | A61C 15/046 132/325 |
| 2006/0011212 A1 * | 1/2006 | Achepohl | A61C 15/046 132/325 |
| 2010/0229888 A1 | 9/2010 | Tiphonnet | |
| 2011/0041870 A1 * | 2/2011 | Kalbfeld | A61C 15/046 132/325 |

* cited by examiner

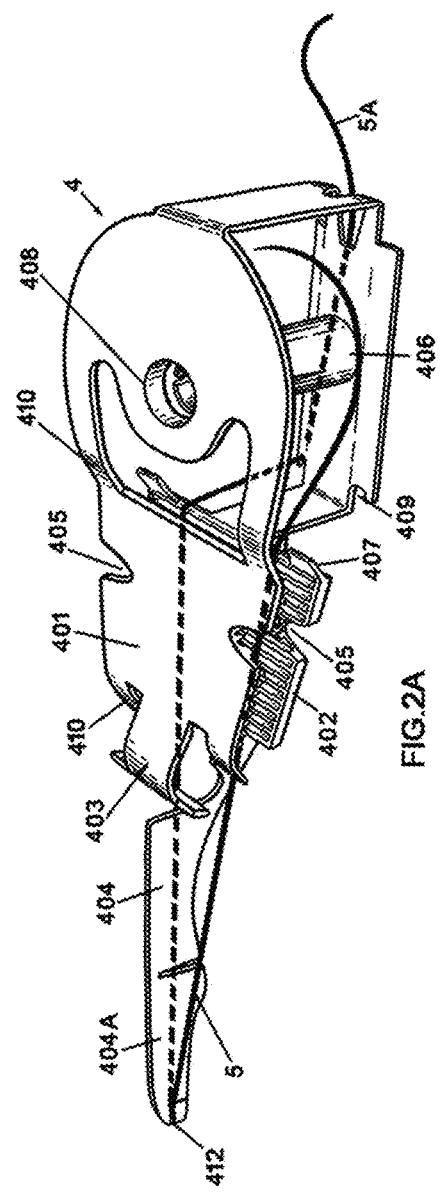
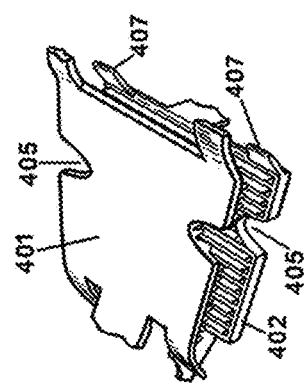

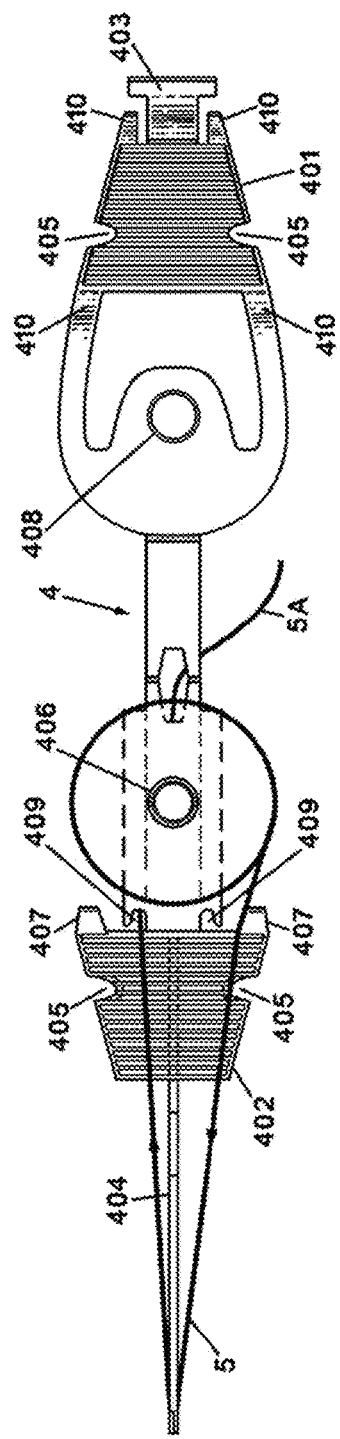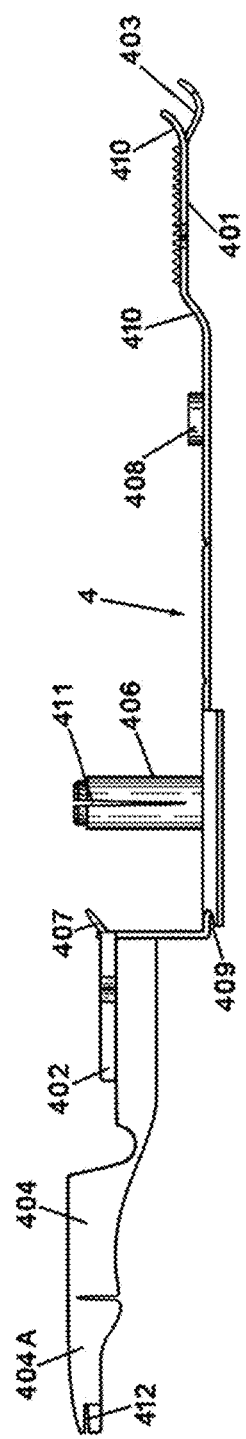

New Features may be released

Most dental floss materials tested don't need waterproof protection.
If necessary, this is the solution:

New design of cassette with waterproof container
for dental floss material

For better protection between a new and used
dental floss material possible to add a wall partition

DENTAL TAPE AND FLOSS HOLDER WITH INSTALLATION CASSETTE

CROSS-REFERENCE TO RELATED APPLICATIONS

The present continuation-in-part patent application claims priority benefit under 35 U.S.C. 120 and 365(c) of the PCT international patent application designating the U.S. Ser. No. PCT/US11/52066, filed 18 Sep. 2011, entitled "Dental Tape and Floss Holder with installation cassette". This application further claims benefit of priority under 35 U.S.C. § 119(e) to U.S. provisional patent application No. 61/403,635, filed Sep. 20, 2010, entitled "Dental Floss Holder with installation cassette," The contents of these related patent application(s) are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to dental care. More particularly, the invention relates to a dental floss holder.

BACKGROUND OF THE INVENTION

The present invention relates to a dental floss holder. Daily flossing is highly recommended by dentists for good oral health. However, many people do not practice daily flossing. Some people do not floss because the floss can be difficult to use as it may break, tangle or pinch the fingers during use. It is therefore an objective of the present invention to provide a device that holds dental floss during use.

Currently, dental floss holders exist. However, when using these dental floss holders it is often difficult to hold the floss firmly in the desired position. Also, the floss may stretch or become tangled during flossing or when removing used floss from the holder. Furthermore, many dental floss holders require the user to install a piece of floss in the holder before each use or are not reusable and are thrown away after one use. Some floss holders accept only limited types of floss and may not be suitable for using dental tape and flosses using modern technologies. Some floss holders require large pieces of floss to be replaced at a time, creating waste. In other floss holders replacing is time consuming and the floss can be tangled or twisted. Yet other floss holders are designed for right hand users and are not as equally convenient for left hand users. Still other floss holders are not designed for easy access to all areas in the mouth.

In view of the foregoing, there is a need for improved techniques for providing a dental floss holder that firmly holds the floss, generally prevents the floss from stretching or becoming tangled and is easily reused.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A is a diagrammatic side view. FIG. 1B is a diagrammatic front view, and FIG. 1C is a diagrammatic rear view;

FIGS. 2A, 2B, 2C and 2D illustrate an exemplary floss cassette from a dental floss holder, in accordance with an embodiment of the present invention. FIG. 2A is a side perspective view of the floss cassette in a closed position. FIG. 2B is a side perspective view of locking plates of the floss cassette, FIG. 2C is a diagrammatic top view of the floss cassette in an open position, and FIG. 2D is a diagrammatic side view of the floss cassette in an open position;

FIG. 3A is a side perspective view. FIG. 3B is a diagrammatic front view, and FIG. 3C is a diagrammatic bottom view;

FIG. 4A is a diagrammatic side view of the floss holder in an open position, and FIG. 4B is a side perspective view of the floss holder in the open position with a locking button, a floss cassette and a blade removed;

Figure 1C:
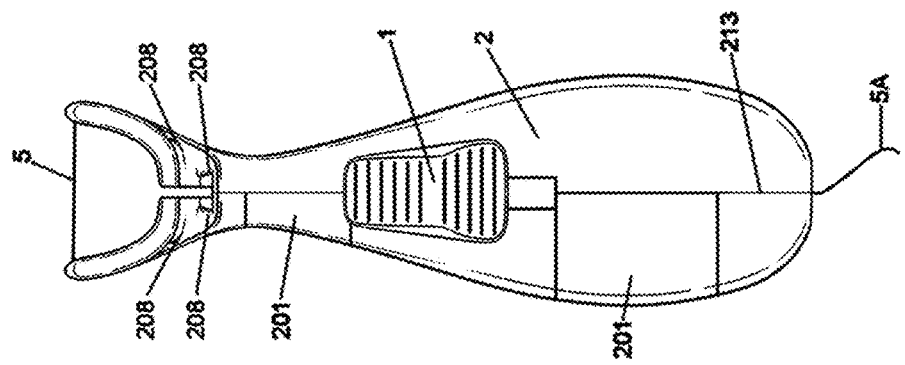
FIGS. 1A, 1B and 1C illustrate an exemplary dental floss holder, in accordance with an embodiment of the present invention.

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub combination. The Applicants hereby give notice that new Claims may be formulated to such features and/or combinations of such features during the prosecution of the present Application or of any further Application derived therefrom.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

A preferred embodiment of the present invention and some variations thereof provide a dental floss holder, which may be used with conventional round floss or dental tape. Some preferred embodiments allow for the use of many types of floss including, but not limited to, round floss, dental tape, flosses using modern technologies developed for new applications of synthetic materials with elastic effect, ultra thin floss, wax covered floss, etc. Some preferred embodiments may be designed to enable them to be produced from plastic with existing technologies used for manufacturing containers for conventional dental flosses and tapes. However, some alternate embodiments may be produced using different techniques and from different materials including, but not limited to, metals, composites, rubber, or a combination of materials. Some preferred embodiments comprise a small number of parts, which allows for quick and easy installation of the floss and generally ensures minimum costs in the production of the device.

Figure 1B:
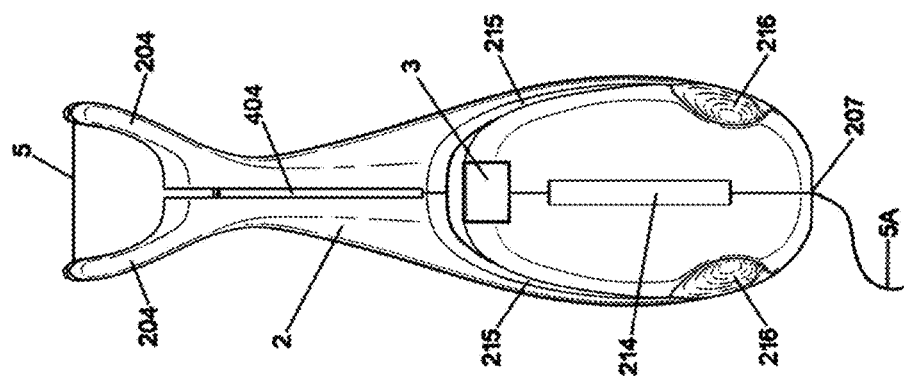
Figure 1A:
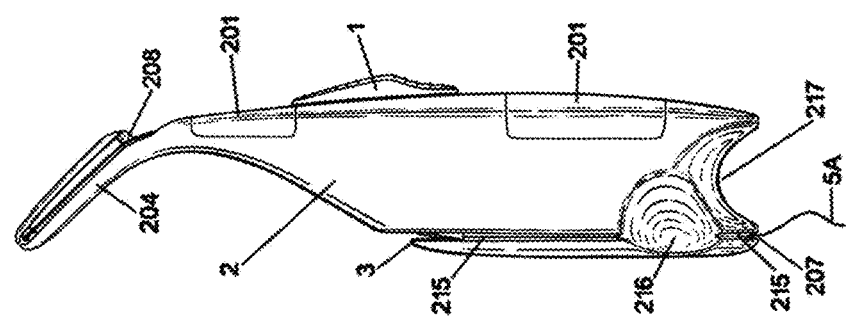

FIGS. 1A, 1B and 1C illustrate an exemplary dental floss holder, in accordance with an embodiment of the present invention. FIG. 1A is a diagrammatic side view. FIG. 1B is a diagrammatic front view, and FIG. 1C is a diagrammatic rear view. In the present embodiment, the floss holder is preferably made for effective use of dental tape. However, the floss holder also allows for the use of conventional round floss, waxed floss, ultra thin floss, synthetic floss, elastic floss, etc. In the present embodiment, the floss holder comprises a housing 2, a floss cassette, as shown by way of example in FIGS. 2A through 2C, a locking button 1, which locks a stretched portion of floss 5 within a locking mechanism in housing 2, and a rounded blade 3. The design of floss holder housing 2 and particularly a fork 204 comprising fork-shaped protruding ends enables smooth flossing by holding a piece of floss 5 firmly in the desired position and generally preventing floss 5 from stretching and tangling during flossing or while removing used floss. Indent 217 on housing 2 enables the user to rest the floss holder on a finger while operating locking button 1 to prevent the floss holder from slipping.

A free end 5A of floss 5 is pulled out through an opening 207, which enables a user to pull floss 5 through the floss holder after housing 2 is locked in a closed position. In the present embodiment opening 207 is located at the end of housing 2 opposite fork 204; however, this opening may be placed in various different locations in alternate embodiments such as, but not limited to, on the front or side of the housing. In the present embodiment, housing 2 is held in place in the closed position with two housing fixating plates 201, which are locked firmly in place with the help of a locking mechanism, shown by way of example in FIG. 4B. To open housing 2, fixating plates 201 are unlocked and the two portions of housing 2 are spread apart along a seam 213 on the back with a hinge 214 on the front. Free end 5A of floss 5, which is the used portion of floss 5, is manually pulled through opening 207 and into a channel 215, which guides free end 5A in the direction of cutting blade 3 where the used portion of floss 5 is cut off. Alternate embodiments may be implemented without a channel for guiding the free end of the floss and also be implemented without a blade. In the present embodiment, protrusions 208, which are also located on the inside of housing 2 as shown by way of example in FIG. 4B, reduce friction on floss 5 in the process of sliding floss 5 through the floss holder when the used portion is replaced with a clean portion. Dimples 216 enable a user to firmly grasp housing 2 when floss 5 is manually pulled through opening 207 and into a channel 215 and capture free end 5A in the process of cutting by the blade 3.

In the present embodiment, the floss holder is designed to allow equally easy operation for left or right-handed users. For example, without limitation, dimples 216 and channels 215 are provided on both sides of housing 2 to enable the used portion of floss 5 to be cut on either side of housing 2. However, alternate embodiments may be implemented as specifically right-handed or left-handed devices. In the present embodiment, the floss holder provides considerable savings of floss since during the replacement of floss 5 on fork 204 only about one to one and a half inches of floss are used. Also, the process of replacing floss 5 is fast and simple, often taking only one to two seconds to complete. The floss holder is designed so that the clean portion of floss 5 does not come into contact with the used portion at any time during flossing or during the replacement of floss 5 on fork 204.

FIGS. 2A, 2B, 2C and 2D illustrate an exemplary floss cassette 4 from a dental floss holder, in accordance with an embodiment of the present invention. FIG. 2A is a side perspective view of floss cassette 4 in a closed position. FIG. 2B is a side perspective view of locking plates 401 and 402 of floss cassette 4. FIG. 2C is a diagrammatic top view of floss cassette 4 in an open position, and FIG. 2D is a diagrammatic side view of floss cassette 4 in an open position. In the present embodiment floss 5 is installed in floss cassette 4 by being coiled around a cylinder 406 then being fed between locking plates 401 and 402 around a plate 404 and a plate portion 404A. In some embodiments, plate portion 404A includes a notch 412, shown in FIG. 4B, to capture floss 5. In other alternate embodiments, various other means may be used to capture floss 5. From here, floss 5 is placed back through locking plates 401 and 402 then into one of notches 409 and out of cassette 4 so that a free end 5A of floss 5 can exit the floss holder once cassette 4 is installed in the floss holder, as shown by way of example in FIG. 4A. Floss cassette 4 comprises a stretching mechanism 403, which holds floss 5 in place and stretches floss 5 on the fork of the floss holder and maintains floss 5 in the stretched position for smooth and easy flossing, as described by way of example in accordance with FIG. 4A. In order for floss 5 to be coiled around cylinder 406, a user may manually wind a long piece of floss around cylinder 406 or a pre-wound spool of floss may be placed on cylinder 406. In some embodiments the cassette may be preloaded with floss. In these embodiments, the user may obtain the cassette preloaded with a type of floss of his/her choosing. During the installation in the present embodiment, protruding segments 407 hold floss 5 in place on locking plate 402. A hole 408 locks the top of cassette 4 upon cylinder 406. Openings 411 enable hole 408 to decrease the diameter of cylinder 406. During installation of the floss roll, tight contact of the floss roll and the cylinder 406 allows convenient installation of the floss on the cassette and prevents the floss on the roll from twisting in the process of floss installation. This reduces the amount of the friction during the replacement of the used portion of floss 5. In alternate embodiments cylinder 406 may not have openings 411. In these embodiments the floss roll does not tightly contact cylinder 406 and during the installation of the floss, the roll is held in place by user's fingers to prevent twisting. In some embodiments cylinder 406 has a top portion with a smaller outside diameter than the rest of the cylinder. This top portion fits into a raised lip of hole 408. After floss 5 is installed in cassette 4, cassette 4 is inserted into the housing of the floss holder. Openings 405 on locking plates 401 and 402 are installed upon protrusions inside the housing, shown by way of example in FIGS. 4A and 4B.

In the present embodiment, locking plates 401 and 402 comprise zigzagged surfaces with a multiplicity of protrusions. In alternate embodiments the zigzagged surface may only be on locking plate 401 or only on locking plate 402. The number of protrusions and corresponding hollow segments on locking plates 401 and 402 depends on the size of the floss holder. In alternate embodiments only one of the locking plates may have a zigzagged surface or the surfaces may have different textures such as, but not limited to, a bumpy or rough texture. Plates 410 on the top portion of cassette 4 and plate 401 provide unlocking of locking plates 401 and 402, as described by way of example in accordance with FIG. 4A.

Figure 3A:
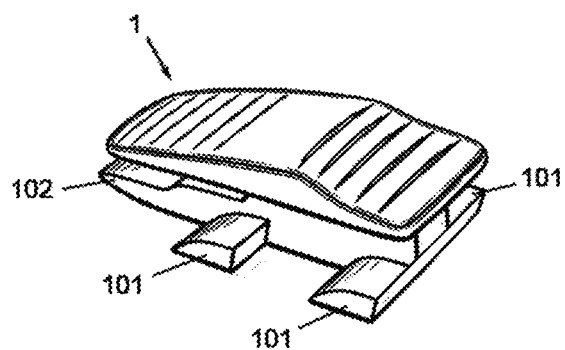
FIGS. 3A, 3B and 3C illustrate an exemplary locking button of a dental floss holder, in accordance with an embodiment of the present invention.
Figure 3B:
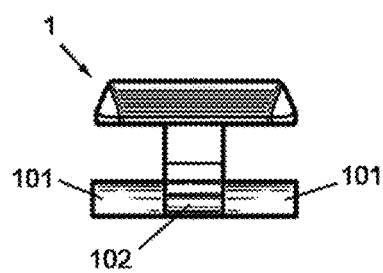
Figure 3C:
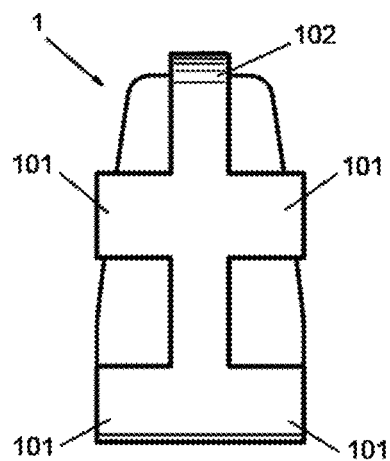

FIGS. 3A, 3B and 3C illustrate an exemplary locking button 1 of a dental floss holder, in accordance with an embodiment of the present invention. FIG. 3A is a side perspective view. FIG. 3B is a diagrammatic front view, and FIG. 3C is a diagrammatic bottom view. In the present embodiment, locking button 1 comprises an irregular bottom surface with protrusions 101 extending from a horizontal element 102. When locking button 1 is installed in the floss holder, pushing down on locking button 1 causes the floss in the floss holder to be held in place.

Figure 4A:
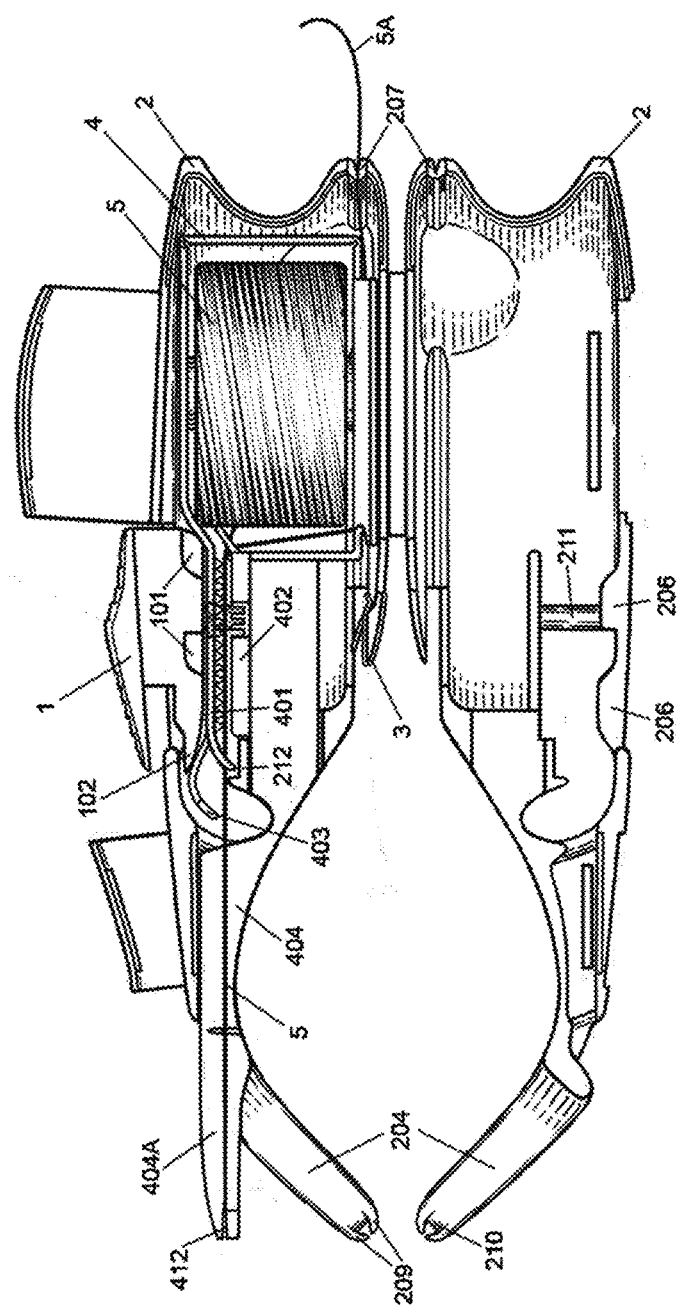
FIGS. 4A and 4B illustrate an exemplary dental floss holder, in accordance with an embodiment of the present invention.
Figure 4B:
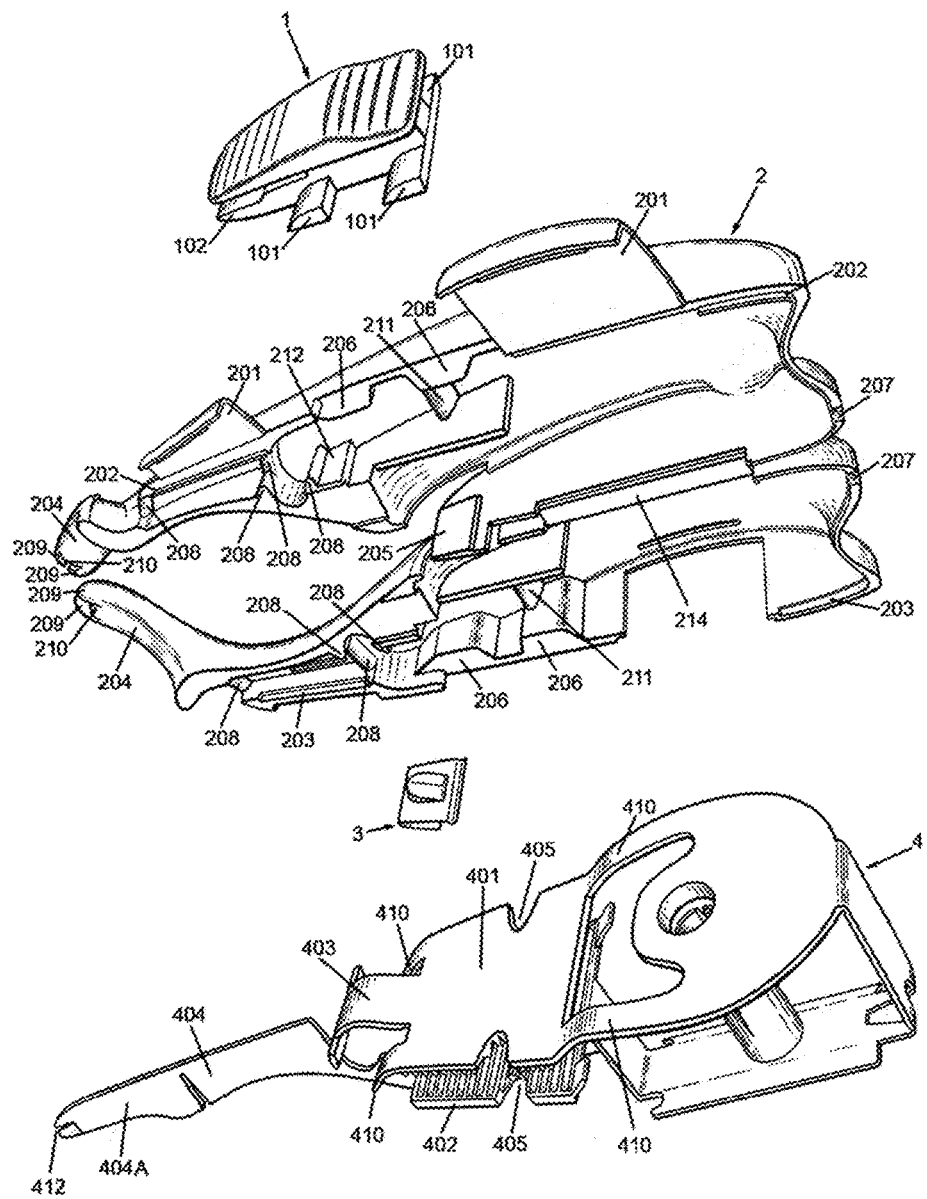

FIGS. 4A and 4B illustrate an exemplary dental floss holder, in accordance with an embodiment of the present invention. FIG. 4A is a diagrammatic side view of the floss holder in an open position, and FIG. 4B is a side perspective view of the floss holder in the open position with a locking button 1, a floss cassette 4 and a blade 3 removed. In the present embodiment, a housing 2 opens by pivoting at a hinge 214. In alternate embodiments, the housing may comprise two halves that are separate from each other that snap together to close. Other alternate embodiments may comprise doors that swing open, slide open, or snap on and off of the housing to provide access to the inside of the housing to load the floss. Referring to FIG. 4A, after the installation of floss 5, cassette 4 is closed and inserted into housing 2 of the floss holder. In the present embodiment, floss cassette 4 is slid into the side of housing 2; however, alternate embodiments may be implemented where the floss cassette is installed in different ways for example, without limitation, dropped in from the top or bottom of the housing. Referring to FIGS. 4A and 4B, in the present embodiment, a protrusion 212 provides stable positioning for plates 410 on the front of cassette 4. Openings 405 on locking plates 401 and 402 of cassette 4 are installed upon protrusions 211 inside housing 2 and hold and stabilize locking plate 401 over locking plate 402.

Once floss cassette 4 is in place, locking button 1 is installed above floss cassette 4. An opening 207 in housing 2 enables a user to pull a free end 5A of floss 5 out of housing 2 so that the used portions of floss 5 can be replaced with clean floss when floss locking plates 401 and 402 are unlocked, as shown by way of example in FIG. 4A. The portion of floss 5 around a plate 404 is installed on a fork 204 of the floss holder once housing 2 is closed. Referring to FIG. 4B, in the closed position, housing 2 is held closed by two fixating plates 201, which are locked firmly in place by locking mechanisms 202 locking into openings 203 on the opposite end of housing 2. Plate portion 404A is removed from plate 404 and discarded after floss 5 is installed on fork 204.

In the present embodiment, the floss holder allows for effective and convenient flossing thanks to a mechanism for locking and stretching floss 5 on fork 204. This mechanism is located on floss cassette 4 and comprises locking plates 401 and 402 with zigzagged surfaces. Referring to FIG. 4A, locking button 1 and locking plates 401 and 402 are shown in an unlocked position. Once housing 2 is closed and floss 5 is placed on fork 204, pushing down locking button 1 causes floss 5 to be locked between locking plates 401 and 402, and sliding locking button 1 towards fork 204 causes a horizontal element 102 of locking button 1 to push down upon a stretching mechanism 403 of floss cassette 4, which results in stretching mechanism 403 being pushed down onto and stretching floss 5 on fork 204 of housing 2. After it is pushed down and slid forward towards fork 204, locking button 1 holds its position and holds plate 401 in place against plate 402 with the help of protrusions 101 located on locking button 1, which engage with protruding elements 206 on the inside of housing 2. This double locking mechanism provides effecting locking of floss 5 between plates 401 and 402 of floss cassette 4 and stretching of floss 5 on fork 204 by virtue of horizontal element 102 pressing upon stretching mechanism 403. In alternate embodiments, the locking mechanism may be actuated by various different means other than a sliding button such as, but not limited to, a push button, a lever, a dial, etc. In the present embodiment to unlock floss 5, locking button 1 is slid away from fork 204 and slides off of protruding elements 206. This releases locking button 1 upward away from plates 401 and 402 and therefore enables plate 401 to move upward, away from plate 402. Plates 410 on the top portion of cassette 4 and plate 401 facilitate the unlocking of locking plates 401 and 402 by Initially plate 401 is located above the plate 402 with a space between the plates 401 and 402 which is needed for smooth removal of the used portion of the floss. In the process of locking, elements 410 bend and provide locking of the floss between the plates. After unlocking, elements 410 return plate 401 to its previous position allowing space to be created for removal of the used portion of the floss.

Referring to FIG. 4B, the openings located on plate 402 of floss cassette 4 generally prevent wax build-up and allow for smooth sliding of floss 5 even when wax-covered floss and dental tape is used. The openings on the plate 402 are aligned with protruding ends of plate 401. This enables protruding ends on the plate 401 to block floss inside the openings of the plate 402. The wax build-up is pushed away under plate 402 thus preventing wax build-up between the plates, which can cause inconvenience to the user in the process of removing used portion of the floss. A multiplicity of protrusions 208 located on housing 2 reduces friction of floss 5 while floss 5 slides through the floss holder in order to replace used floss with clean floss. Alternate embodiments may be implemented without these protrusions. In the present embodiment, rounded blade 3, used for cutting off used floss, is located on the lower portion of housing 2 on a blade plate 205. As shown in FIG. 1A, this location of blade 3 enables blade 3 to be recessed from the bottom surface of housing 2 for the user's safety while leaving a sufficient length of floss outside housing 2 for easy grasping. However, the cutting blade may be located in various different locations in alternate embodiments such as, but not limited to, near the opening from which the floss exits the floss holder, and other alternate embodiments may be implemented without a blade. In the present embodiment, fork 204, which is formed when housing 2 is closed, comprises extensions 209 that form a hollow shape which allows for the installation of floss 5 on fork 204 and holds floss 5 in place during flossing. The rounded shape of ends 210 of fork 204 facilitates smooth sliding of floss 5 and generally prevents twisting or breaking during use. Those skilled in the art will readily recognize, in accordance with the teachings of the present invention that the forks in alternate embodiments may vary in shape. For example, without limitation, the ends of the fork may comprise holes into which the floss is threaded, or the ends may comprise shallow grooves into which the floss is placed. In some embodiments the ends of the fork may be made of rubber or may be covered by rubber tips to protect the mouth of the user and to more securely grip the floss.

In typical use of the present embodiment, which is illustrated by way of example in FIGS. 1A through 4B, a user opens housing 2 of the floss holder along seam 213 and inserts a loaded floss cassette 4 into housing 2, as shown by way of example in FIG. 4A. Then, the user installs locking button 1 above locking plates 401 and 402 and closes housing 2 by locking fixating plates 201. The user then pulls floss 5 wrapped around plate 404 and plate portion 404A from the floss holder and inserts floss 5 between extensions 209 on fork 204. Once floss 5 is installed on fork 204, the user may break off plate portion 404A. To tighten and lock floss 5 in place, the user then slides locking button 1 toward fork 204. The user may now hold the floss holder in either hand to use the portion of floss 5 in fork 204 to floss his teeth.

In order to replace the used portion of floss 5 with an unused portion, the user slides locking button 1 away from fork 204 to unlock locking plates 401 and 402 and pulls on free end 5A to slide floss 5 through the floss holder and out opening 207. Once the used portion of floss 5 is pulled out of fork 204, the user slides locking button 1 back toward fork 204 to lock the clean portion of floss 5 in place. If desired, the user may then take free end 5A of floss 5 up through channel 215 to cut off the excess floss with blade 3. Those skilled in the art will readily recognize, in accordance with the teachings of the present invention, that any of the foregoing steps may be suitably replaced, reordered, removed and additional steps may be inserted depending upon the needs of the particular application. For example, without limitation, locking button 1 may be installed before floss cassette 4, and the user may skip the step of cutting the excess floss from free end 5A.

An alternate embodiment of the present invention may provide a floss holder that does not use a floss cassette. In this embodiment, the locking mechanism is built into the housing of the floss holder along with floss holding means. A user installs the floss directly into the housing and feeds the floss through the built in locking mechanism prior to use.

Figure 5:
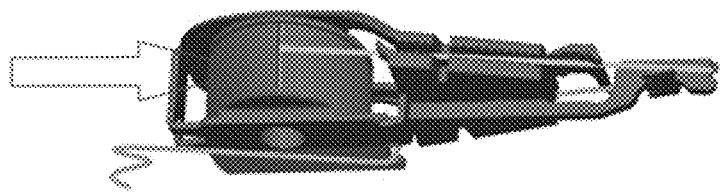
FIG. 5 illustrates an exemplary water resistant dental floss holder, in accordance with an alternative embodiment of the present invention. The dental floss holder in FIG. 5 includes a water resistant container which helps avoid water penetration to the dental floss held within the water resistant container; and, FIG. 6 illustrates an exemplary dental floss holder having a wall partition member, in accordance with an alternative embodiment of the present invention. The dental floss holder in FIG. 6 includes a wall partition member which helps provide a better partition between new and used dental floss material.

FIG. 5 illustrates an exemplary water resistant dental floss holder, in accordance with an alternative embodiment of the present invention. The dental floss holder in FIG. 5 includes a water resistant container which helps avoid water penetration to the dental floss held within the water resistant container.

Figure 6:
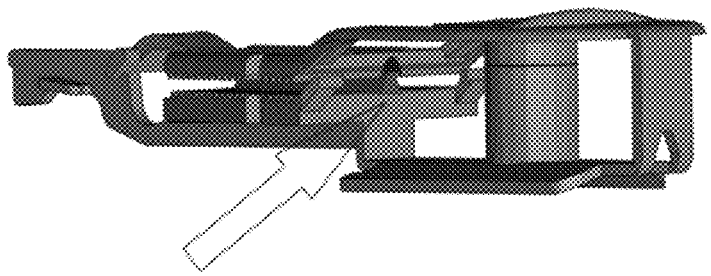

FIG. 6 illustrates an exemplary dental floss holder having a wall partition member, in accordance with an alternative embodiment of the present invention. The dental floss holder in FIG. 6 includes a wall partition member which helps provide a better partition between new and used dental floss material.

Those skilled in the art will readily recognize, in accordance with the teachings of the present invention, that various features of the floss holder illustrated by way of example in the foregoing may vary in alternate embodiments. For example, without limitation, the forks in alternate embodiments may have various different shapes such as, but not limited to, square forks, the housings may have various different shapes including, but not limited to, housings with finger grooves for improved grip or rectangular housings, floss holders in alternate embodiments may come in various different sizes for example, without limitation, adult and children's sizes, etc. Furthermore, there are various protrusions illustrated in the foregoing embodiment for guiding the floss and reducing friction. In alternate embodiments the number and locations of these protrusions may vary greatly, and some embodiments may be implemented without these protrusions. Yet other alternate embodiments may comprise additional features such as, but not limited to, a dental pick, a tongue scraper, an electric motor to provide vibration, etc.

Having fully described at least one embodiment of the present invention, other equivalent or alternative methods of providing a floss holder according to the present invention will be apparent to those skilled in the art. The invention has been described above by way of illustration, and the specific embodiments disclosed are not intended to limit the invention to the particular forms disclosed. For example, the particular implementation of the floss cassette may vary depending upon the particular type of floss used. The floss spools described in the foregoing were directed to relatively short implementations; however, similar techniques are to provide floss cassettes to accommodate floss spools of various different sizes such as, but not limited to, tall spools or wide spools. In some of these implementations, the configuration of the floss within the cassette may vary depending on the size of the spool in order to fit the floss within the floss holder; for example, without limitation, the spool may be held in the cassette vertically rather than horizontally. Implementations of the present invention for use with different sizes of floss spools are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A dental floss holder comprising:
    (a) a housing comprising a first part and a second part together forming in a closed position a fork having two prongs with the first part carrying only one of said two prongs and the second part carrying only the other of said two prongs with the two prongs receiving a feed portion of floss and an aperture on a side of the housing opposite the fork for enabling a return portion of floss to exit the housing;
    (b) a spindle or spool contained in the housing, said spindle or spool receiving a quantity of floss wound thereabout;
    (c) a first toothed locking plate disposed in, and being a separate structure from, the housing, said first toothed locking plate receiving the feed portion with the return portion returning back over a substantially horizontal and toothed surface of the first toothed locking plate;
    (d) a second toothed locking plate disposed in, and separate from, the housing and the second toothed locking plate is positioned between the first toothed locking plate and a locking button disposed in the housing, said locking button protruding through the housing so as to enable selective locking of the feed portion and the return portion of the floss by a user, wherein teeth of the first locking plate and teeth of the second locking plate are selectively engaged together by a user moving the locking button towards the fork, whereby a distal end of the second toothed locking plate proximate to the fork engages the feed portion of the floss with the return portion of the floss returning back over the substantially horizontal surface of the first toothed locking plate and a substantially horizontal and toothed surface of the second toothed locking plate to substantially restrain the feed portion and the return portion between the first toothed locking plate and the second toothed locking plate, wherein the act of moving the locking button towards the fork applies a tension force to the feed portion between the two prongs of the fork and applies a tension force to the return portion; and
    (e) a cutting blade connected to the housing for cutting the return portion.

2. The dental floss holder of claim 1, wherein the locking button includes a plurality of protrusions that lodge between and thereby engage protruding elements of the housing when the locking button is selectively moved towards the fork.

3. The dental floss holder of claim 2, wherein each of the plurality of protrusions are wedge-shaped.

4. The dental floss holder of claim 1, wherein the housing includes a plurality of housing protrusions on the first part and a plurality of housing protrusions on the second part, about which floss moves, creating a plurality of contact points between the floss and the housing, thereby reducing friction between the floss and the housing.

5. The dental floss holder of claim 4, wherein one of the plurality of housing protrusions on the first part is disposed at the base of the fork and wherein one of the plurality of housing protrusions on the second part is symmetrically disposed on the other side of the base of the fork.

6. The dental floss holder of claim 1, wherein each prong of the fork includes an end for facilitating the smooth movement of floss between the prongs.

7. The dental floss holder of claim 1, wherein each prong of the fork includes a pair of extensions having a space between each of the pair of extensions, each said pair of extensions being positioned to retain the floss during inserting, removing, and flossing.

8. The dental floss holder of claim 7, wherein the space between each of the pair of extension enables a user to reposition floss between prongs of the fork if the floss tears or slips.

9. The dental floss holder of claim 1, wherein the cutting blade is recessed below a surface of the housing.

10. The dental floss holder of claim 1, wherein the locking button is a sliding button.

11. The dental floss holder of claim 1, wherein the distal end of the second toothed locking plate includes at least one notch for securing the feed portion or the return portion.

12. The dental floss holder of claim 1, wherein the first part or the second part includes a plurality of fixating plates holding together the first part and the second part.

13. The dental floss holder of claim 1, wherein the housing includes a seam between the first part and the second part, said seam acting as a hinge or pivot, and wherein the housing is selectively openable by a user to install or replace the quantity of floss by pivoting the first part away from the second part.

14. A dental floss holder comprising:
(a) a housing comprising a first part and a second part together forming in a closed position a fork having two prongs receiving a feed portion of floss and an aperture on a side of the housing opposite to the fork for enabling a return portion of floss to exit the housing, wherein each prong of the fork includes a channel for passing the feed portion and the return portion;
(b) a floss cassette contained in and being a separate structure from the housing, said cassette having a first part including a locking hole connected to a first toothed locking plate, said first toothed locking plate receiving both the feed portion and the return portion over a substantially horizontal and toothed surface of the first toothed locking plate, and a second part including a vertical spindle that receives a spool of floss with the spool comprising the feed portion and the return portion with the spindle and locking hole coupling together to form an open container holding the spool of floss and a second toothed locking plate is connected to the spindle, said second toothed locking plate being positioned between the first toothed locking plate and a locking button disposed in the housing, said locking button protruding through the housing so as to enable selective locking of the feed portion and the return portion by a user, wherein teeth of the first locking plate and teeth of the second locking plate are selectively engaged together by a user by moving the locking button towards the fork, whereby a distal end of the second toothed locking plate proximate to the fork engages the feed portion of the floss with the return portion of the floss returning back over the substantially horizontal surface of the first toothed locking plate and a substantially horizontal and toothed surface of the second toothed locking plate to substantially restrain the feed portion and the return portion between the first toothed locking plate and the second toothed locking plate, wherein the act of moving the locking button towards the fork applies a force to the first toothed locking plate and the second toothed locking plate and applies a tension force to both the feed portion between the two prongs of the fork and the return portion; and
(c) a cutting blade connected to the housing for cutting the return portion.

15. The dental floss holder of claim 14, wherein each prong of the fork includes a pair of extensions having a space between each of the pair of extensions, each said pair of extensions being positioned to retain the floss during inserting, removing, and flossing and wherein the space between each of the pair of extensions enables a user to reposition floss between prongs of the fork if the floss tears or slips.

16. The dental floss holder of claim 14, wherein the cutting blade is recessed below a surface of the housing.

17. The dental floss holder of claim 14, wherein the locking button is a sliding button.

18. The dental floss holder of claim 14, wherein the first part or the second part includes a plurality of fixating plates holding together the first part and the second part.

19. The dental floss holder of claim 14, wherein the housing includes a seam between the first part and the second part, said seam acting as a hinge or pivot and wherein the housing is selectively openable by a user to install or replace the spool of floss by pivoting the first part away from the second part.

20. The dental floss holder of claim 14, wherein the distal end of the second toothed locking plate includes at least one notch for securing the feed portion or the return portion.

\* \* \* \* \*